(12) United States Patent
Adeyeye et al.

(10) Patent No.: US 6,566,347 B1
(45) Date of Patent: May 20, 2003

(54) CONTROLLED RELEASE PHARMACEUTICAL

(75) Inventors: Christianah Moji Adeyeye, Mt. Lebanon, PA (US); Ashwinkumar C. Jain, Pittsburgh, PA (US)

(73) Assignee: Duquesne University of the Holy Ghost, Pittsburgh, PA (US)

( * ) Notice: Subject to any disclaimer, the term of this patent is extended or adjusted under 35 U.S.C. 154(b) by 0 days.

(21) Appl. No.: 09/934,883

(22) Filed: Aug. 22, 2001

(51) Int. Cl.⁷ .................. A01N 43/04; A61K 31/715
(52) U.S. Cl. ................ 514/58; 514/54; 514/57; 536/56; 536/58; 536/103; 536/123.1
(58) Field of Search ............... 514/54, 57, 58; 536/56, 58, 103, 123.1

(56) References Cited

U.S. PATENT DOCUMENTS

| | | | |
|---|---|---|---|
| 4,596,795 A | | 6/1986 | Pitha |
| 6,218,375 B1 | * | 4/2001 | Raghavan et al. ............ 514/58 |
| 6,358,935 B1 | * | 3/2002 | Beck et al. .................. 514/58 |
| 2002/0035264 A1 | * | 3/2002 | Kararli et al. .............. 546/300 |

OTHER PUBLICATIONS

"Characterization and Bioavailability of Danazol–Hydroxypropyl β–Cyclodextrin Derivatives", *International Journal of Pharmaceutics*, vol. 128, pp. 45–54 (1996) Sherif I. F. Badawy et al.

"Bioavailability of Danezol–Hydroxypropyl-β-Cyclodextrin Complex by Different Routes of Administration", *International Journal of Pharmaceutics*, vol. 145, pp. 137–143 (1996). Sherif I. F. Badawy et al.

"Bioavailability of Testosterone Using a Bioadhesive Tablet with Penetration Enhancers in Dogs", *World Meet, Pharm. Technol.*, 1st, pp. 179–180 (1995), J. Voorspeels, et al.

* cited by examiner

*Primary Examiner*—James O. Wilson
*Assistant Examiner*—Patrick Lewis
(74) *Attorney, Agent, or Firm*—Craig G. Cochenour; Buchanan Ingersoll (57) ABSTRACT

The present invention provides a controlled release pharmaceutical composition comprising a polydextrose, a drug that is complexed with the polydextrose, and a polymer matrix having the drug complexed with the polydextrose, wherein the polymer matrix and the polydextrose provide for a time release of the drug. A method of therapeutically treating a patient for an illness employing the controlled release pharmaceutical composition is also provided.

11 Claims, 5 Drawing Sheets

FIG. 1

In vitro dissolution profiles of various formulations prepared using danazol SBE 7Beta-CD complexes and Polycarbophil (FIG. 2A) and HPMC K15M (FIG. 2B) (The formulations are listed in Table 2).

FIG. 2A

In vitro dissolution profiles of various formulations prepared using danazol SBE 7Beta-CD complexes and Polycarbophil (FIG. 2A) and HPMC K15M (FIG. 2B) (The formulations are listed in Table 2).

Plot of mean amount of plasma danazol following drug administration via the peroral route for Danocrine® capsules (200 mg danazol) and danazol-SBE 7Beta CD complex buccal tablets (40 mg danazol).

FIG. 4

CONTROLLED RELEASE PHARMACEUTICAL

BACKGROUND OF THE INVENTION

1. Field of the Invention

This invention relates to a controlled release pharmaceutical composition that achieves a slow release of drug over an extended period of time and a method of therapeutically treating a patient with an illness employing the controlled release pharmaceutical composition.

2. Brief Description of the Background Art

Danazol is a synthetic androgen that inhibits the output of pituitary gonadotropins. Danazol is neither estrogenic or progestational and it depresses the output of both follicle stimulating hormone and luteinizing hormone. It is used in the treatment of endometriosis at a recommended therapeutic dose of 600–800 milligrams/day (mg/day) in two divided doses. In the treatment of fibrocystic breast disease, the therapeutic dose of danazol ranges from 100–400 mg/day in two divided doses. At a starting dose of 200 mg 2–3 times a day it is used in the management of migraine headaches. These high doses of danazol are required because the bioavailability of commercially available danazol is very low. The low bioavailability is due to the low solubility of danazol in aqueous medium and due to first pass hepatic metabolism, all well known by those skilled in the art. The high dose of danazol used in various therapies causes side effects such as weight gain, virilism, and decreased bone mineral content.

It is known to provide orally administrable drugs in tablet form for buccal administration to circumvent hepatic metabolism of the drug. The bioavailability of hepatically metabolized drugs, such as for example, but not limited to steroids, can be improved by buccal dosing. The buccal route of administration does not expose the drug to the metabolic enzymes on first passing via the intestines and through the liver during absorption.

Prior studies involving the oral, sublingual and buccal administration of steroids have been performed. *Characterization and bioavailability of danazol-hydroxypropylβ-cyclodextrin coprecipitates*, International Journal of Pharmaceutics, Vol. 128, pages 45–54 (1996), authored by Sherif I. Farag Badawy, Mahmoud M. Ghorab, and Christianah Moji Adeyeye (present Applicant), hereinafter referred to as Badawy I, describes the preparation and study of danazol complexed with aqueous hydroxypropyl β-cyclodextrin (HPCD) solutions and administered via the oral route (non-buccally). Badawy I shows that the orally (non-buccally) administered danazol HPCD complex has increased solubility and higher dissolution rates in comparison to the commercially available oral (non-buccal) formulation of danazol (Danocrine®, Sterling-Winthrop Pharmaceuticals, New York, N.Y.). Badawy I states that although both the danazol HPCD complex and Danocrine® showed relatively low absolute bioavailability due to presystemic elimination of danazol, the danazol HPCD complex showed a higher rate and extent of absorption via gavage administration over the commercially available formulation of Danocrine®. Badawy I does not concern itself with overcoming the problems associated with buccal administration of drugs.

*Bioavailability of danazol-hydroxypropyl-β-cyclodextrin complex by different routes of administration*, International Journal of Pharmaceutics, Vol. 145, pages 137–143 (1996), Sherif I. Farag Badawy, Mohmoud M. Ghorab, and Christianah Moji Adeyeye (present Applicant), hereinafter referred to as Badawy II, discloses the bioavailability of danazol HPCD complex using buccal and oral routes of administration. Badawy II employed a buccal administration of danazol via a rapidly dissolving adhesive patch. The adhesive patch was composed of danazol HPCD complex, hydroxypropyl cellulose/polycarbophil (carbopol 934)/polyethylene glycol (PEG) 400 in a 63.75:28.4:2.5:5.35 weight ratio. Badawy II states that the buccal absorption of danazol HPCD in the patch formulation across the mucosa was slow and the absorption phase long. Badawy II concluded that administration of the danazol HPCD complex in the rapidly dissolving patch formulation did not result in adequate buccal absorption of danazol and that further investigation was needed to allow for adequate buccal absorption.

U.S. Pat. No. 4,596,795 (Pitha) discloses the sublingual route of administration of steroids complexed with hydrophilic beta-cyclodextrin derivatives, namely hydroxypropyl betacyclodextrin (HPCD).

*Bioavailability of testosterone using a bioadhesive tablet with penetration enhancers in dogs*, World Meet. Pharm., Biopharm. Pharm. Technol., 1st, pages 179–80 (1995), J. Voorspoels, et al., hereinafter referred to as Voorspoels et al., discloses the administration of sodium taurodehydrofusidate, sodium deoxycholate, or hydroxypropyl beta cyclodextrin (HPCD) with testosterone in a buccal dosage form. Voorspoels et al. states that the use of HPCD did not improve the buccal administration of the steroid testosterone.

In spite of this background art, there remains a very real and substantial need for a controlled release pharmaceutical composition having greater bioavailability as provided by the instant invention for the therapeutic administration of drugs that effectively bypass presystemic metabolism and result in administration of a substantially lower dose to the patient.

SUMMARY OF THE INVENTION

The present invention has met the hereinbefore described needs. The present invention provides a controlled release pharmaceutical composition comprising a water soluble polydextrose, a drug that is complexed with the water soluble polydextrose, and a polymer for forming a polymer matrix having the drug complexed with the water soluble polydextrose, wherein the polymer matrix and the water soluble polydextrose provide for a time release of the drug.

More specifically, the present invention provides for a controlled release pharmaceutical composition, as described herein, wherein it is preferable that the drug is of low water solubility, and most preferably is a drug that is a practically water-insoluble drug as defined in the United States Pharmacopeia XXII (hereinafter "USP"). The USP defines "practically insoluble" as 10,000 and over parts of solvent required for 1 part of solute.

Preferably, the present invention provides a controlled release pharmaceutical composition comprising a water soluble polydextrose, a steroid complexed with the water soluble polydextrose, and a polymer for forming a polymer matrix having the steroid complexed with the water soluble polydextrose wherein the polymer matrix and the water soluble polydextrose provide for a time release of the drug to the buccal mucosa of a patient. Most preferably, the instant invention as described herein, is a controlled release pharmaceutical composition wherein the water soluble polydextrose is sulfobutylether 7 beta cyclodextrin, the drug is danazol, and the polymer is hydroxypropyl methylcellulose K15M or polycarbophil.

Another embodiment of this invention provides a method for employing the controlled release pharmaceutical composition, as described herein, for therapeutically treating a patient in need of steroid administration. Such patients may present with an illness, such as for example, but not limited to, endometriosis, fibrocystic breast disease, and migraine headache.

DETAILED DESCRIPTION OF THE INVENTION

The present invention involves increasing solubility of drugs, such as for example, but not limited to, steroids, by complexing the drug with sulfobutylether 7β-cyclodextrin (SBE 7β-CD). These inclusion complexes (SBE 7β-CD complex) when delivered by buccal route increase bioavailability, leading to reduced dose of the drug and subsequently lower toxicity. Cyclodextrin's (CD) are cyclic oligosaccharides capable of forming inclusion complexes (hereinafter "complex") with many drugs by including a whole drug molecule, or some non-polar part of drug molecule into its cavity. This is possible because of the hydrophilic outer surface and the hydrophobic central cavity of cyclodextrins. These non-covalent complexes between drugs and cyclodextrin are advantageous in increasing the solubility of drugs and subsequent bioavailability. The use of cyclodextrins for oral applications is appropriate in cases of drugs exhibiting dissolution-limited bioavailability.

Bioavailability of hepatically metabolized drugs (such as steroids) can be substantially improved by buccal dosing, since when administered by these routes the drug is not exposed to the metabolic enzymes of the intestines and the liver during absorption. The drug on contact with the buccal mucosa permeates across the mucosal tissue to reach systemic circulation. The buccal mucosa is easily accessible for the delivery of drugs. An additional advantage of the buccal mucosa is its tolerance (in comparison with nasal and pulmonary mucosae) to potential sensitizers.

The instant invention provides a controlled release pharmaceutical composition comprising a water soluble polydextrose, a drug complexed with the water soluble polydextrose, and a polymer for forming a polymer matrix having the drug complexed with the water soluble polydextrose, wherein the polymer matrix and the water soluble polydextrose provide for a time release of the drug.

In a preferred embodiment of this invention, danazol was complexed with sulfobutylether 7β-cyclodextrin (SBE 7β-CD) to form a danazol sulfobutylether 7β-cyclodextrin complex (hereinafter SBE 7β-CD complex), and buccal tablets having the SBE 7 β-CD complex were prepared using polymers as described herein. The tablets were then evaluated for mucoadhesion and in-vitro release of danazol. The buccal bioavailability of the tablets was evaluated in vivo in female beagle dogs.

Danazol-SBE 7 β-CD complexes (1:20 weight/weight (w/w)) were prepared by solvent evaporation method using 90% methanol as the solvent and were characterized with X-ray diffraction and DSC (Differential Scanning Calorimetry). Buccal tablets were compressed on a Carver® press at 6000 lb. f. (pounds force) using concentrations of two different polymers, namely, Polycarbophil (commercially available as Noveon® AA1, B. F. Goodrich Specialty Chemicals, Cleveland, Ohio) hereinafter "PC", and hydroxypropylmethylcellulose K15M, (commercially available as Methocel K15M Premium CR, Dow Chemical Co., Midland, Mich.) hereinafter HPMC K15M (see Example 2). Tablet dissolution was carried out by USP Type 2 (United States Pharmacopeia Type 2) method. Phosphate buffer pH 6.8 was used as a dissolution medium in all cases. Mucoadhesion was measured using a Chatillon® tension tester. (See Example 3). In Example 4, in vivo bioavailability was performed in four female beagle dogs using IV danazol (2 mg/kg), peroral danazol- SBE 7β-CD complex (50 mg), buccal tablet danazol SBE 7β-CD (40 mg danazol), and peroral commercial formulation of danazol, Danocrine® (200 mg). X-ray diffraction showed the disappearance of characteristic crystalline peaks of danazol, indicating amorphous nature of danazol in the SBE 7β-CD complexes. DSC thermograms of complex showed the disappearance of the peak of fusion of danazol, indicating complexation. About 85% of danazol was released from the complex of the present invention in 15 minutes as compared to 5% in the corresponding physical mixture of danazol and SBE 7β-CD. As the concentration of the polymer (polycarbophil or HPMC K15M) increased drug release from the tablets decreased. The rate of drug release from tablets containing HPMC K15M was higher compared to polycarbophil tablets. Tablets made with polycarbophil showed greater mucoadhesion compared to HPMC K15M containing tablets. The $C_{max}$ for Danocrine® (124.99±82.06 nanograms/milliliter (ng/ml)) was significantly lower than for the perorally administered complex (2057.19±1046.95 ng/ml), p=0.01. The absolute oral bioavailability of Danocrine® was only 1.8%, significantly lower than the absolute bioavailability of the complex of the present invention administered orally (64%) or as a sustained release tablet of the complex administered buccally (25%). Absorption of danazol from the buccal tablets was much slower and extended over a longer period of time compared to peroral Danocrine®. The relative bioavailability of danazol complex or the buccal tablets was enhanced 33 times or 13 times respectively compared with Danocrine®.

The following examples further illustrate the present invention. β-cyclodextrin is a product of enzymatic degradation of starch and contains seven glucose units joined in a circle by alpha (1–4) glycosidic bonds. Sulfobutylether 7β-cyclodextrin (SBE 7β-CD) is a derivative of β-cyclodextrin, and is more soluble in water and is a better solubilizer than parent β-cyclodextrin. Sulfobutyl ether β-cyclodextrins are a mixture of positional and regional isomers containing from one to as many as twelve sulfobutyl ether groups per cyclodextrin (CD). These mixtures are generally characterized by an average degree of substitution calculated on the basis of elemental analysis and/or nuclear magnetic resonance data. The number following the abbreviation "SBE" refers to the average number of substituted sulfobutyl ether groups per CD, such as for example, the number "7".

EXAMPLE 1

Various concentrations of SBE 7 β-CD were used to determine the solubility of danazol as described in Table 1.

TABLE 1

Solubility of danazol in various concentrations of SBE 7 β-CD solutions at two different temperatures.

| SBE 7β-CD mM (millimole) | Solubility of danazol in mM (millimole) | |
|---|---|---|
| | 22° C. (centigrade) | 37° C. |
| 0 | 0.0009 | 0.00181 |
| 0.05 | 0.003 | 0.004 |
| 0.1 | 0.008 | 0.009 |
| 0.25 | 0.03 | 0.04 |
| 0.5 | 0.06 | 0.08 |
| 1 | 0.12 | 0.15 |

EXAMPLE 2

Figure 1:
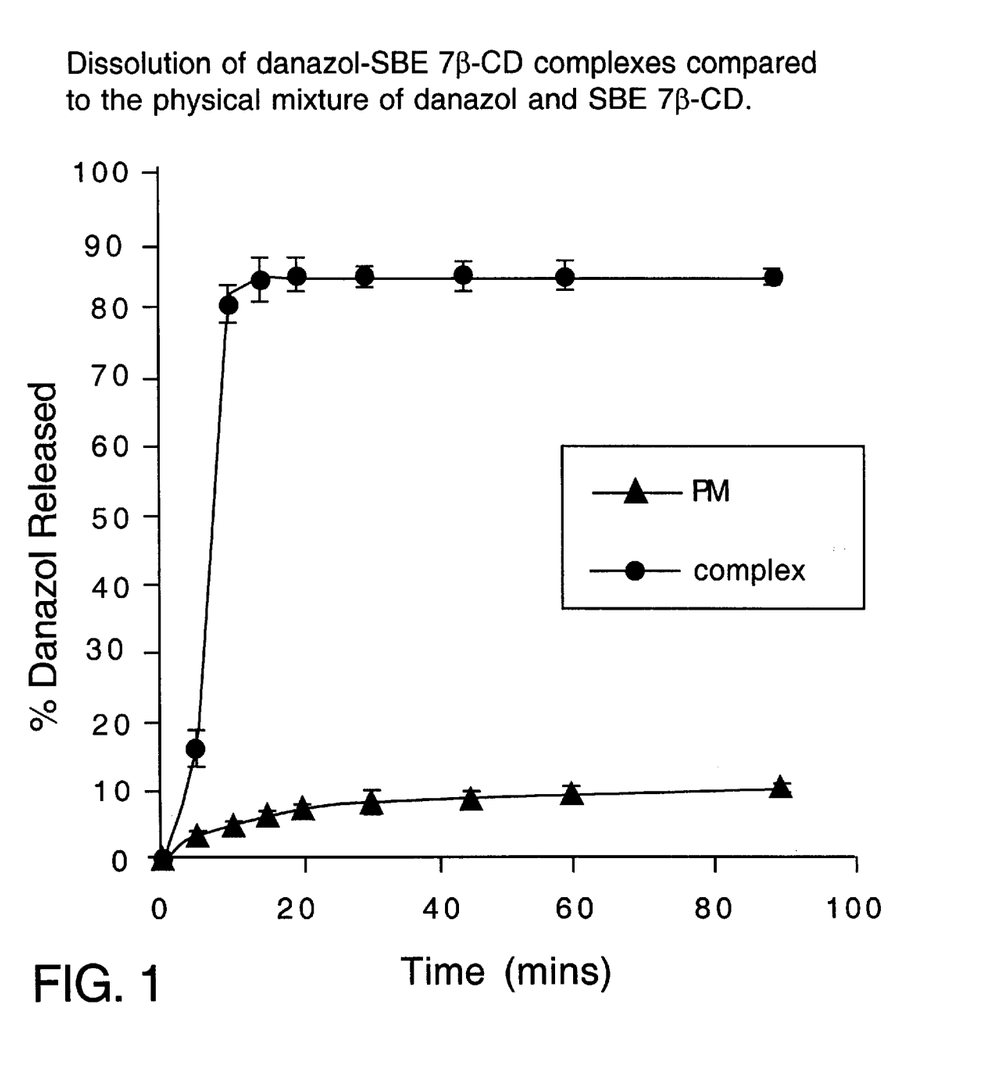
FIG. 1 shows the amount of danazol released over time from the dissolution of the danazol-SBE 7 β-CD complex of the instant invention compared to the dissolution of a physical mixture of danazol and SBE 7 β-CD.

The complexes of the steroids with SBE 7 β-CD were obtained by the solvent evaporation method known by those skilled in the art. Briefly, danazol (1 mole) and SBE 7β-CD (3 moles) were dissolved in 90% methanol separately and then the two solutions were mixed. The solutions were stirred at ambient temperature and evaporated to dryness. The resulting danazol SBE 7β-CD complexes which are in the form of a white amorphous powder were screened through a #100 sieve and stored in a desiccator. For comparison purposes, physical mixtures were also prepared by physically mixing danazol with SBE 7β-CD. FIG. 1 shows that the solubility of the complexes of the present invention are greatly enhanced compared to the physical mixtures (PM).

EXAMPLE 3

Danazol -SBE 7 β-CD complex equivalent to 40 mg of danazol was mixed with known polymers (polycarbophil and HPMC K 15M) and triturated in a mortar. Tablets (average weight 830 milligram (mg) were compressed on a Carver® press at a force of 6000 lb.f. (pound force) for 15 seconds. Various examples of formulations of the complexes of the present invention are shown in Table 2. The tablets were stored in a desiccator until further used. Mucoadhesion of these tablets was studied using cellulose acetate membrane dipped in mucin solution as known by those skilled in the art.

Figure 2A:
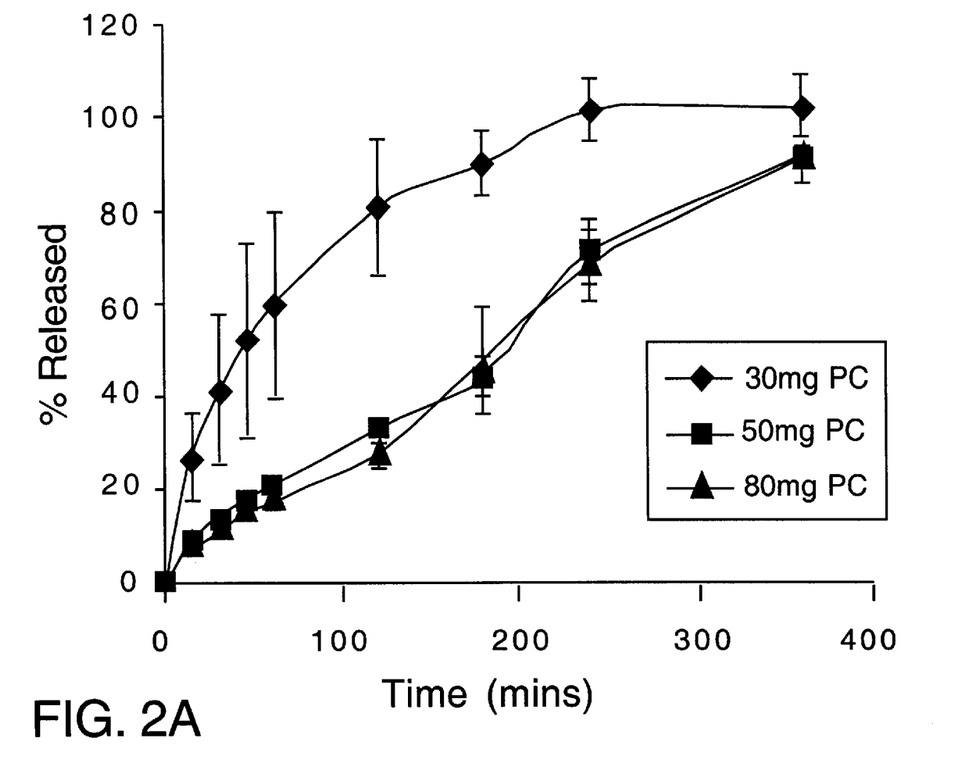
FIG. 2 shows the in vitro dissolution profiles of various formulations of the controlled release pharmaceutical compositions of the instant invention.
Figure 2B:
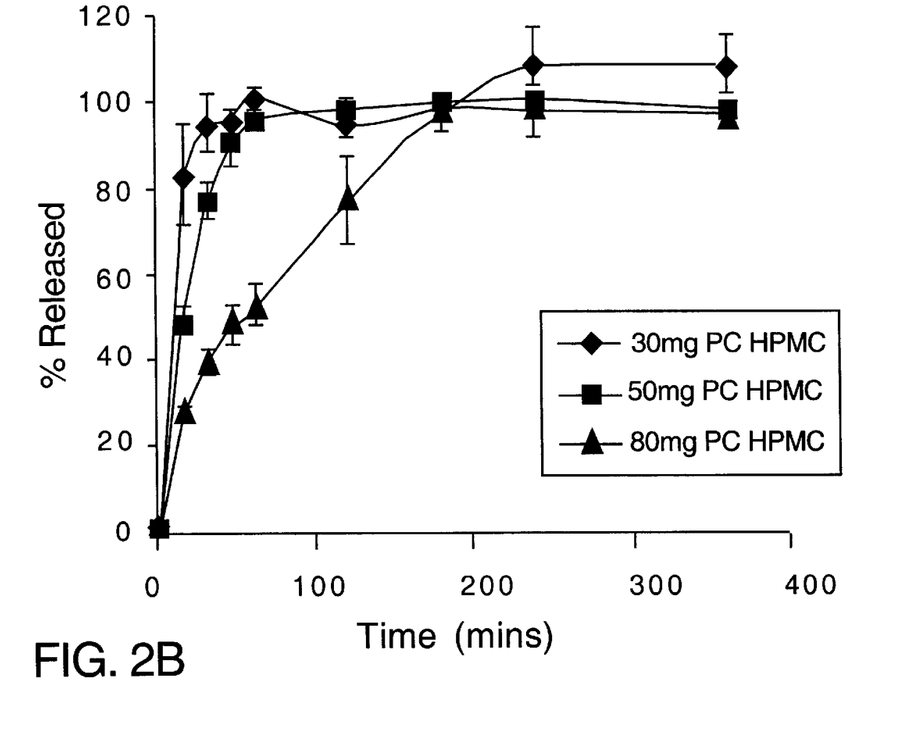

All formulations of Table 2 (I–VI) demonstrated controlled release behavior as shown in FIG. 2. In general, as the concentration of the polymers (both polycarbophil and HPMC K15M) increased, danazol release from the tablets decreased. However, the rate of danazol release from tablets containing water soluble HPMC K15M (i.e., formulations IV, V and VI) was higher compared to water insoluble polycarbophil (PC) containing tablets (i.e., formulations I–III). Table 2 generally shows that as the concentration of polymers increased, the mucoadhesion increased (average force of detachment increased). The formulations of the present invention containing polycarbophil showed greater mucoadhesion compared to formulations containing HPMC K15M (Table 2).

TABLE 2

Mucoadhesive data of buccal tablets containing danazol SBE 7β-CD-complex equivalent to 40 mg danazol

| Formulation | Polymer type | Polymer Concentration (mg) | Average force of Detachment (N) |
|---|---|---|---|
| I | PC | 30 | 3.91 (1.24) |
| II | PC | 50 | 5.41 (1.28) |
| III | PC | 80 | 5.91 (0.49) |
| IV | HPMC K15M | 30 | 2.50 (0.45) |
| V | HPMC K15M | 50 | 4.41 (1.24) |
| VI | HPMC K15M | 80 | 4.16 (1.63) | n = 6. Values in the parentheses represents standard deviations.

EXAMPLE 4

Four healthy female beagle dogs (average weight 9.2 kilograms (kg)) were used as experimental animals in this in vivo study. The dogs were fasted overnight prior to the administration of the dosage forms. During all the experiments water was available ad libitum and food was given 6 hours after the dose of drug was administered. A minimum of one-week washout period was allowed between each dosing.

For buccal dosing the dogs were anaesthetized with propofol and maintained on isoflurane or halohane for 2 hours to allow adhesion of buccal tablets. One tablet containing 40 mg of danazol in the danazol SBE 7β-CD complex of formulation I (Table 2) was placed on the lower gum of each dog. Twenty minutes post-dosing, each dog was administered approximately 0.8 milliliter (ml) of atropine to maintain heart rate. Blood samples (2.5 ml) were withdrawn from the cephalic or jugular vein just prior to (blank plasma), and 0.5, 1,2,4,6, 8 and 24 hours after tablet application. Plasma samples were stored and assayed as specified above. Dogs were fed after six hours.

In order to determine, if complexation with sulfobutylether 7β cyclodextrin (SBE 7β-CD) improves the bioavailability of danazol, the dogs were administered perorally (non-bucally) with SBE 7β-CD complex equivalent to 50 mg of danazol. Also each dog was dosed perorally with Danocrine® capsules (200 mg) with the aim of determining the bioavailability of danazol itself. Intravenous dosing (2 mg/kg body weight) was also performed using danazol dissolved in a mixture of polyethylene glycol 400 and propylene glycol (1:1).

Pharmacokinetic evaluation of the danazol detected in plasma was done using WinNonlin®v. I.I (commercially available from Scientific Consulting Inc., North Carolina). All the plasma concentration versus time profiles were subjected to compartmental model independent analysis. The area under the concentration time curve (AUC) from t=0 to the time of the last blood sample was determined by the linear trapezoidal rule, well known by those skilled in the art.

Figure 3:
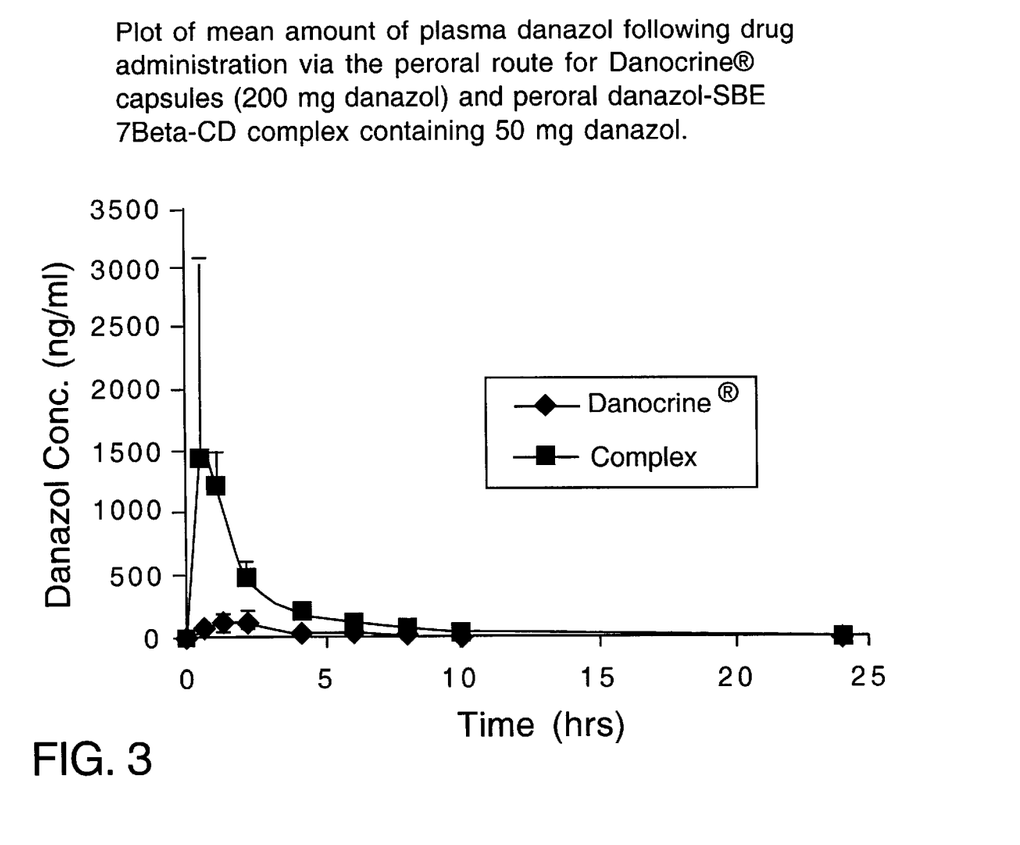
FIG. 3 shows the mean amount of plasma danazol concentration via the peroral route for Danocrine® capsules in comparison to peroral route (non-buccal) for the danazol-SBE 7β-CD complex of the instant invention.

FIG. 3 represents the plot of mean amount of plasma danazol following drug administration via the peroral route for Danocrine® capsules (200 mg danazol) and the peroral route (non-buccal) for danazol—SBE 7β-CD complex containing 50 mg danazol of the present invention. Three of the four dogs showed similar plasma danazol concentrations, while for one dog the plasma danazol concentration was very high. Table 4 shows the various pharmacokinetic parameters. Compared to the peroral administration of Danocrine® ($C_{max}$ of 124.99±82.06 nanogram/milliliter (ng/ml)) a higher $C_{max}$ of 2057.19±1046.95 ng/ml was observed for the perorally administered danazol SBE 7β-CD complex. Also a shorter $t_{max}$ 0.75±0.29 hour (hr) for the danazol SBE 7β-CD complex was seen compared to peroral Danocrine®. This higher $C_{max}$ and a shorter $t_{max}$ are a result of increased solubility of danazol upon complexation with sulfobutylether 7β-cyclodextrin of the present invention. The absolute bioavailability F, of the peroral danazol SBE 7β-CD complex was 63.86% compared to peroral Danocrine® of 1.88%. Thus, the relative bioavailability of peroral danazol was enhanced 33 times upon complexation with SBE 7β-CD compared with commercially available danazol (Danocrine®).

Figure 4:
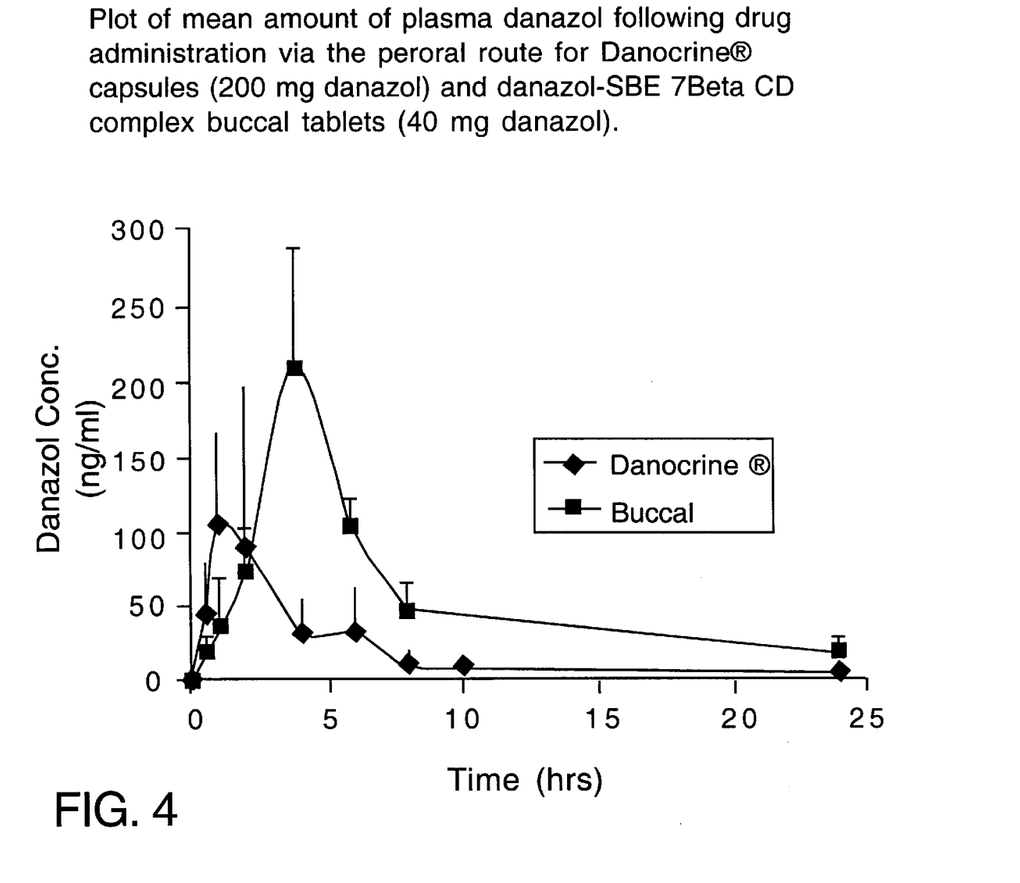
FIG. 4 shows the mean amount of plasma danazol concentration via the peroral route for Danocrine® capsules in comparison to the buccal administration of the danazol-SBE 7β-CD complex of the instant invention.

FIG. 4 shows that the absorption of the danazol SBE 7β-CD complex of the present invention from buccal tablets was much slower and extended over a longer period of time compared to peroral Danocrine® and the peroral danazol SBE 7β-CD complex. Table 4 shows that for the danazol SBE 7β-CD complex buccal tablets of the present invention, the time for maximum concentration $t_{max}$ (4 hrs) was higher compared to peroral Danocrine® and the peroral danazol SBE 7β-CD complex of the present invention. However, the $C_{max}$ was significantly lower (210.57±79.18 ng/ml) for the SBE 7β-CD complex buccal tablets of the present invention compared to peroral danazol SBE 7β-CD of the present invention. Absolute bioavailability of buccally administered danazol SBE 7β-CD complex tablet was 25% and relative bioavailability of the buccal tablets was 13 times higher than that of Danocrine®. The increased bioavailability of danazol upon administration as a buccal tablet complexed with SBE 7 β-CD is due to (i) increased solubility upon complexation and (ii) potential avoidance of first pass hepatic metabolism since danazol is not exposed to the metabolic enzymes of the intestines and the liver during buccal absorption. Since the absolute bioavailability of both the danazol SBE 7β-CD complex buccal tablets and peroral danazol SBE 7β-CD complex of the present invention is greater than the commercially available Danocrine®, a lower dose of danazol can be used in danazol therapy employing the present invention. Further, it will be appreciated by those skilled in the art that employing the controlled release pharmaceutical compositions of the present invention will reduce the various side effects of danazol associated with use of higher doses as described earlier.

TABLE 4

Pharmacokinetic parameters following administration of various formulations to fasted female beagle dogs (n = 4, values in the parentheses are standard deviations).

| Formulations | Cmax (ng/ml) | tmax (hr) | AUC 0–24 hr (ng h/ml)* | F % (Absolute bioavail.) | Relative bio-availability |
|---|---|---|---|---|---|
| Intravenous | — | — | 2154.64 (417.80) | 100 | — |
| Danocrine ® Capsule (200 mg) | 124.99 (82.06) | 1.13 (0.63) | 40.57 (30.44) | 1.88 | — |
| Complex capsule (50 mg) | 2057.19 (1046.95) | 0.75 (0.29) | 1376.00 (303.61) | 63.86 | 33.90 |
| Buccal tablet (40 mg) | 210.57 (79.18) | 4.00 (0.00) | 554.95 (133.13) | 25.76 | 13.70 |

*AUC values normalized to 2 mg/kg dog weight

The relative bioavailability is the ratio of the absolute bioavailabilities of the Complex capsule or Buccal tablet to Danocrine® Capsule.

It will be appreciated by those skilled in the art that the polydextrose of the present invention may also be for example, but not limited to, alpha, beta, and gamma cyclodextrins, hydroxypropyl-beta-cyclodextrin, hydroxypropyl-gamma-cyclodextrin and sulfobutylether-gamma-cyclodextrin.

It will be understood by those skilled in the art that the drug of the present invention may be any drug, and preferably is a drug having low solubility, and most preferably is a drug which is practically insoluble as defined by the USP XXII. Such drugs also include those classes of drugs, known by those skilled in the art to be hepatically metabolized and/or having low water solubility.

In the present invention, the polymer is one which gives controlled release properties as understood by those skilled in the art, such as for example, but not limited to polyvinylpyrrolidone, hydroxypropylcellulose, hydroxypropylmethylcellulose, polycarbophil, and mixtures of these polymers with bioadhesive polymers well known by those skilled in the art.

It will be appreciated by those skilled in the art that the controlled release pharmaceutical compositions of this invention may be employed to deliver a drug to a patient to provide therapy for an illness. The illness may be for example, but not limited to, endometriosis, infertility, hereditary angioedema, autoimmune diseases, premenopausal abnormal bleeding, migraine headaches, and metastatic and fibrocystic breast disease.

Whereas, particular embodiments of this invention have been described herein for purposes of illustration, it will be evident to those skilled in the art that numerous variations of the details of the present invention may be made without departing from the invention as defined in the appended claims.

We claim:

1. A controlled release pharmaceutical composition comprising:
   a water soluble polydextrose comprising a sulfobutylether β-cyclodextrin;
   a drug complexed with said water soluble polydextrose; and
   a polymer for forming a polymer matrix having said drug complexed with said water soluble polydextrose, wherein said polymer matrix and said water soluble polydextrose provide for a time release of said drug in a buccal dosage form.

2. The controlled release pharmaceutical composition of claim 1 wherein said drug is a steroid.

3. The controlled release pharmaceutical composition of claim 2 wherein said steroid is danazol.

4. The controlled release pharmaceutical composition of claim 1 wherein said polymer of said polymer matrix is hydroxypropyl methylcellulose K15M.

5. The controlled release pharmaceutical composition of claim 1 wherein said polymer of laid polymer matrix is polycarbophil.

6. The controlled release pharmaceutical composition of claim 2 wherein the ratio of steroid to polymer is from about 1:1 to 1:2 weight/weight.

7. The controlled release pharmaceutical composition of claim 2 including wherein the ratio of said steroid to said sulfobutylether β-cyclodextrin is 1:20 on a weight/weight basis.

8. The controlled release pharmaceutical composition of claim 2 including wherein the ratio of said steriod to said sulfobutylether β-cyclodextrin is 1:3 on a mole/mole basis.

9. The controlled release pharmaceutical composition of claim 1 that is a solid dosage form for buccal administration.

10. A method of therapeutically treating a patient for an illness responsive to steroid administration wherein the illness is at least one selected from the group consisting of endometriosis, infertility, hereditary angioedema, autoimmune disease, premenopausal abnormal bleeding, migraine headaches, and metastatic and fibrocystic breast diseases comprising:

employing a controlled release pharmaceutical composition comprising a water soluble polydextrose comprising a sulfobutylether β-cylcodextrin; a drug comprising a steroid complexed with said water soluble polydextrose; and a polymer for forming a polymer matrix having said drug complexed with said water soluble polydextrose, wherein said polymer matrix and said water soluble polydextrose provide for a time release of said drug in a buccal dosage form;

administering a therapeutically effective amount of said controlled release pharmaceutical composition to a patient by the buccal route; and     employing said method in treating a patient to provide therapy for said illness.

11. The method of claim 10 including wherein said steroid is danazol.

* * * * *

UNITED STATES PATENT AND TRADEMARK OFFICE
CERTIFICATE OF CORRECTION

PATENT NO.    : 6,566,347 B1
DATED         : May 20, 2003
INVENTOR(S)   : Christianah Moji Adeyeye and Ashwinkumar C. Jain It is certified that error appears in the above-identified patent and that said Letters Patent is hereby corrected as shown below:

<u>Column 8,</u>
Line 54, change "laid" to -- said --.

Signed and Sealed this

Fourth Day of November, 2003

JAMES E. ROGAN
*Director of the United States Patent and Trademark Office*